United States Patent [19]
Baer et al.

[11] Patent Number: 5,321,331
[45] Date of Patent: Jun. 14, 1994

[54] DOUBLE-SIDED FLUID SENSOR FOR REDUCED ATTENUATION OF SHEAR TRANSVERSE WAVES

[75] Inventors: Richard L. Baer; Curt A. Flory, both of Los Altos, Calif.

[73] Assignee: Hewlett-Packard Company, Palo Alto, Calif.

[21] Appl. No.: 852,365

[22] Filed: Mar. 13, 1992

[51] Int. Cl.$^5$ .......................................... H01L 41/08
[52] U.S. Cl. ........................ 310/313 D; 73/24.01; 73/24.06; 73/64.53; 73/61.79; 310/313 B
[58] Field of Search ............... 73/24.06, 64.53, 61.79, 73/61.75, 31.05, 24.01, 599; 310/313 B, 313 R, 313 D

[56] References Cited

U.S. PATENT DOCUMENTS

| | | | |
|---|---|---|---|
| 4,361,026 | 11/1982 | Muller et al. | 73/23 |
| 4,636,678 | 1/1987 | Ballato | 310/313 D |
| 4,814,658 | 3/1989 | Suthers et al. | 310/313 D |
| 4,837,476 | 6/1989 | Mochizuki | 310/313 R |
| 4,918,349 | 4/1990 | Shiba et al. | 310/313 C |
| 4,965,479 | 10/1990 | Elliott et al. | 310/313 D |
| 5,076,094 | 12/1991 | Frye et al. | 73/24.06 |
| 5,111,168 | 5/1992 | Panasik et al. | 310/313 D |
| 5,117,146 | 5/1992 | Martin et al. | 310/313 B |
| 5,187,980 | 2/1993 | Blair et al. | 73/599 |
| 5,220,234 | 6/1993 | Flory et al. | 310/313 D |

OTHER PUBLICATIONS

Wenzel et al., "Flexural Plate-wave Gravimetric Chemical Sensor," *Sensors and Actuators*, A21-A23 (1990), pp. 700-703.

Martin et al., "Characterization of SH Acoustic Plate Mode Liquid Sensors," *Sensors and Actuators*, 20 (1989), pp. 253-268.

D. F. Thompson, "Temperature Compensation of Microwave Acoustic Resonators," doctoral dissertation for Stanford University, Jun. 1986, Chapter III.

C. Caliendo et al. "K+ detection using shear horizontal acoustic modes", IEEE 1990 Ultrasonics Symposium vol. 1, Dec. 4, 1990, pp. 383-387.

*Primary Examiner*—Hezron E. Williams
*Assistant Examiner*—Rose M. Finley

[57] ABSTRACT

A fluid sensing device such as a Surface Transverse Wave device or a Love Wave device having controlled transfers of energy from a transduction surface of a piezoelectric substrate to a sensing surface and back to the transduction surface. A first wave-trapping structure adjacent to an input transducer tapers to provide a controlled diffraction of shear transverse wave energy to a second wave-trapping structure disposed on an opposite side of the piezoelectric substrate. The second wave-trapping structure interfaces with the fluid under test. The shear transverse waves are then recaptured by a third wave-trapping structure on the same surface as the first wave-trapping structure. The wave energy is then decoupled from the piezoelectric substrate. In the STW device, the wave-trapping structures are periodic fingers that are selectively varied in thickness or width or both. In the LW device, the wave-trapping structures are plates that each vary in thickness.

17 Claims, 3 Drawing Sheets

DOUBLE-SIDED FLUID SENSOR FOR REDUCED ATTENUATION OF SHEAR TRANSVERSE WAVES

TECHNICAL FIELD

The present invention relates generally to Shear Transverse Wave and Love Wave devices and more particularly to increasing the sensitivity of a fluid sensor by reducing device-imposed attenuation of shear transverse waves.

BACKGROUND ART

There are a number of types of piezoelectric devices that have been designed to perform electronic signal processing or to measure such variables as mass, pressure, viscosity and density. For example, a gravimetric sensor may be used to measure the concentration of a selected class of compounds in a chemical solution into which the sensor is immersed. In addition to use with liquids, piezoelectric sensors may be utilized with gases.

As used herein, such piezoelectric devices are broadly classified as "bulk wave devices," "plate wave devices" and "surface wave devices." A bulk wave device is one in which an acoustic wave tends to propagate and extend throughout the full thickness of a piezoelectric substrate. A plate wave device is one in which acoustic energy is confined by reflection from the top and bottom surfaces of a plate. A surface wave device is one in which acoustic energy is confined in a vertical direction (i.e. a direction perpendicular to a substrate surface) in a region adjacent to the substrate surface.

Each of the three classes can be subclassified by the orientation of the acoustic wave motion with regard to the substrate surface of the device. The three types of wave motion are: (1) longitudinal wave motion in which material displacement is in a direction parallel to the direction of propagation of the wave; (2) shear vertical wave motion in which material displacement is in a direction perpendicular to both the substrate surface and the direction of wave propagation; and (3) shear transverse, or shear horizontal, wave motion in which material displacement is perpendicular to the direction of propagation and parallel to the substrate surface.

A "Surface Acoustic Wave" (SAW) device is one type of surface wave device. This type is also known as a "Rayleigh Wave" (RW) device and utilizes waves that are predominantly shear vertical, with the energy localized within an acoustic wave length of the substrate surface. While this type operates efficiently in many applications, the shear vertical wave motion may adversely affect performance when the SAW device is used as a sensor in a liquid. The shear vertical component of wave motion presses against the fluid under test. If the surface wave velocity is greater than the fluid compressional wave velocity, energy will be radiated into the fluid. Because the energy of the surface wave leaks away into the fluid, the fluid compressional waves are called "leaky waves." The attenuation resulting from leaky-wave radiation into a fluid causes an unacceptable amount of insertion loss, rendering the device inoperable for such use.

A "Flexural Plate Wave" (FPW) device also utilizes shear vertical wave motion. An FPW sensor has a thin plate that is fabricated by using conventional semiconductor fabrication techniques. An FPW chemical sensor is described by Wenzel et al. in "Flexural Plate-wave Gravimetric Chemical Sensor," *Sensors and Actuators*, A21–A23 (1990), pages 700–703. A region for the flow of a vapor or a liquid is etched into a silicon substrate and an ultrasonic delay line consisting of a composite plate of low-stress silicon nitride, aluminum and zinc oxide is used as the plate for the top-to-bottom reflection of wave energy. The FPW sensor has the advantage of exhibiting an acoustic velocity that is less than the acoustic velocity of most liquids, thereby avoiding the "leaking away" of wave energy into the liquid. However, the FPW sensor is overly sensitive to small changes in liquid density, pressure and temperature. Moreover, the sensor is relatively fragile, since the plate is extremely thin, as necessitated by a low acoustic velocity.

Shear transverse wave motion is the preferred orientation of acoustic wave motion within a fluid sensor. Shear transverse waves are not affected by the same leaky wave mechanism, since the material displacement at the fluid/substrate interface is parallel to the substrate surface and does not press against the fluid. The absence of the surface-normal component of material displacement allows the shear transverse waves to propagate without unacceptable amounts of wave energy dissipation into the fluid under test.

An "Acoustic Plate Mode" (APM) liquid sensor using shear transverse waves is described by Martin et al. in "Characterization of SH Acoustic Plate Mode Liquid Sensors," *Sensors and Actuators*, 20 (1989), pages 253–268. Martin et al. teach use of a thin, single-crystalline quartz plate which acts as an acoustic wave guide to confine acoustic energy between upper and lower surfaces of a plate as the waves propagate from an input to an output transducer. The upper and lower surfaces of the quartz plate impose a transverse resonance condition, such that the APM has displacement maxima at the surfaces, with sinusoidal variation between the surfaces. Because of the characteristics of plate wave devices, sensing can take place on a side of the quartz plate opposite to the transducers. APM sensors are less susceptible to leaky-wave attenuation, but are typically less sensitive than SAW devices.

A "Surface Skimming Bulk Wave" (SSBW) device utilizes shear transverse wave motion. The Surface Skimming Bulk Wave type is also referred to as a "Shallow Bulk Acoustic Wave" (SBAW) device. Propagation occurs by way of bulk mode, in which the waves graze the surface and diffract into the piezoelectric substrate. Bulk propagating modes have higher velocities than Rayleigh waves, but are more susceptible to losses due to inefficient coupling of power to and from the substrate. Moreover, diffraction losses are significant.

"Love Wave" (LW) devices differ from an SSBW by the inclusion of a plate that functions as a surface trapping structure to trap the wave energy proximate to the surface of the piezoelectric substrate. Addition of the plate provides mass loading and causes piezoelectric shorting which slows down the skimming bulk shear wave, thereby creating a decay of the wave function into the depth of the substrate. The material selected in fabricating the plate is conventionally one having a lower acoustic shear wave velocity than the piezoelectric substrate, so that the plate slows the shear transverse wave even further.

A "Surface Transverse Wave" (STW) device also utilizes shear horizontal wave motion. The STW device differs from the Love Wave device only by the replacement of the wave-trapping plate with surface grooves or with a raised grating of fingers. The grating of fingers provides stronger surface trapping than the plate. Thus, high velocity bulk modes are further trapped near the surface of the substrate, allowing an even greater coupling of power through more efficient transduction.

Typically, an LW sensor or an STW sensor includes an input interdigital transducer having an array of interleaved electrode fingers to launch shear transverse waves along a sensing region of a piezoelectric substrate in response to an electrical signal. On the opposite end of the sensing region is an output interdigital transducer, which detects the waves and generates a corresponding output signal. In its simplest form, such sensors act as highly sensitive detectors of changes in surface mass, responding to accumulated mass per unit area. More sophistication is achieved by coating the surface of the piezoelectric substrate with a chemically reactive layer that preferentially reacts with a constituent within the fluid under test. Depending upon the concentration of the constituent within the fluid, the mass of the chemically reactive layer will fluctuate. The change in mass of the layer causes a corresponding change in the phase delay or acoustic shear wave velocity of the sensor. Thus, the sensor may be dedicated to detection of a specific constituent, such as a particular antibody within a solution.

One concern in the use of an LW sensor or an STW sensor is the effect of the fluid under test on the input and output interdigital transducers. Typically, the electrode fingers of each of the transducers are interleaved metallic members. Depending upon the fluid under test, the fluid may cause corrosion of the electrode fingers. Moreover, the fluid may electrically short the electrode fingers together. Therefore, preferably the fluid is sealed within the sensing region of the sensor and prevented from reaching the interdigital transducers. For example, a flow cell may be mounted to the surface of the piezoelectric substrate and a compliant gasket may be sandwiched between the flow cell and the substrate surface.

Sealing the fluid flow from the interdigital transducers solves the problems of electrical shorting and premature corrosion, but creates other problems. Firstly, the compliant gasket is another source of leaky-wave attenuation. Wave energy leaks away from the sensor substrate into the compliant gasket in the form of shear waves. Secondly, in addition to leaky-wave attenuation, other mechanisms cause the gasket to reflect or absorb wave energy, leaving a smaller fraction of wave energy propagating from the input interdigital transducer to the output interdigital transducer. The wave attenuation increases with the length and the mechanical rigidity of the gasket or other sealing member. Consequently, the choice of the means for providing a fluid-tight seal represents a compromise between attenuation and fluid sealing considerations. That is, the compromise is between the sensitivity of the sensor and the reliability of the seal.

It is an object of the present invention to improve the sensitivity and performance of Surface Transverse Wave devices and Love Wave devices that are utilized for fluid sensing, wherein the improvement is achieved without compromising the reliability of a fluid-tight seal for containment of a fluid under test.

SUMMARY OF THE INVENTION

The above object has been met by a fluid sensing device in which shear transverse wave energy is tightly surface trapped at a sensing region and at regions proximate to input and output transducers, but which allows first and second transfers of wave energy from a transduction surface to a sensing surface of the device. The transfers of wave energy are achieved by a controlled relaxation of surface trapping, allowing the sensing region to be on a side of a piezoelectric substrate opposite to the input and output transducers. Consequently, the interface of the fluid with the device can be restricted to the sensing surface that is on the opposite side of the substrate from the transducers. For purposes of this application, "transduction surface" is defined as the side of the piezoelectric substrate having the input and output transducers, while "sensing surface" is defined as the side of the piezoelectric substrate at which fluid sensing occurs.

In a first embodiment, the fluid sensing device is a Surface Transverse Wave device having arrays of grooves or fingers that function as wave-trapping structures. Either the heights or the widths of periodic perturbations, such as fingers or grooves, may be selectively varied. The height of a finger is defined as the thickness of material as measured from the surface of the piezoelectric substrate. A thick finger yields tight trapping that allows efficient electromechanical coupling between the piezoelectric substrate and the transducer and allows tight surface trapping of wave energy at the sensing region. Thus, the wave-trapping structure should be thickest at areas near the transducers and within the sensing region. A first array of fingers is proximate to the input transducer and tapers in height with departure from the transducer. As the height is decreased, shear transverse waves penetrate deeper into the bulk of the piezoelectric substrate. A second array of fingers is on the opposite, or sensing, surface. The fingers on the sensing surface increase in height to a maximum at a central sensing region and then decrease to allow the wave energy to be transferred back to the transduction surface for detection at the output transducer. A third array of fingers is proximate to the output transducer. The heights of the fingers within the third array increase with approach to the output transducer.

An alternative tapering mechanism for controlling the transfer of wave energy from the input transducer to the sensing surface and for recapturing the wave energy for detection at the output transducer involves the width-to-spacing ratio of the fingers or grooves of the first embodiment. Tapering the width-to-spacing ratio is preferred to a tapering of height, since conventional fabrication techniques do not readily allow highly controlled variations in thickness. Changes in width for a given center-to-center distance, i.e. periodicity, of fingers or grooves will affect surface trapping. An array of wide fingers more tightly traps wave energy to a substrate surface. In the same manner as the tapering of the height, the width-to-spacing ratio of fingers within a first array is gradually decreased with departure from the input transducer. A second array that is disposed on the sensing surface has a gradually increasing ratio at opposed ends and a maximum ratio at a central sensing region. A third array has fingers that increase in width to provide a gradual increase in the width-to-spacing ratio with approach to the output transducer on the transduction surface.

Another alternative tapering mechanism is to combine the tapering of height and width to maximize the range of variation. A fourth alternative is to selectively vary the periodicity, but this is the least desirable of the alternatives since the period is preferably fixed in order to restrict the effects of Bragg scattering to a small range of frequencies.

In a second embodiment, the sensing device is a Love Wave device. The thicknesses of three wave-trapping plates, that take the place of the three arrays of fingers described above, are selectively varied in the same manner as the thickness, or height, of fingers of the STW device. The thickness of two wave-trapping plates on the transducer surface are at a maximum in areas adjacent to the transducers and taper in a manner to efficiently and controllably transfer wave energy to and from a wave-trapping plate on the sensing surface of the LW device.

An advantage of the present invention is that the segregation of transduction and sensing on opposite sides of the piezoelectric substrate permits an improvement in the sensitivity of an STW or LW device without reducing the reliability of a fluid-tight seal. Typically, a flow cell is attached to the surface of the substrate opposite to the transducers. The flow cell is sealed by means of a member which attaches to the substrate surface beyond the second array of fingers of an STW device or beyond the second wave-trapping plate of an LW device. Another advantage is that the present invention simplifies the design of the device and simplifies the choice of materials in forming a seal. In the prior art single-side devices, a gasket which sealed the flow of fluid from the transducers was located in the path of the shear transverse waves. The placement, composition and dimensions of the member which sealed fluid flow from the transducers on a single-sided device were all important design factors to be considered in avoiding excessive wave attenuation. These considerations limited the available choices of materials for forming the seal member, making it difficult to find a material that was compatible with the chemistry under test. The present invention avoids this problem by placing the seal member outside of the path of the shear transverse waves.

BEST MODE FOR CARRYING OUT THE INVENTION

Figure 1:
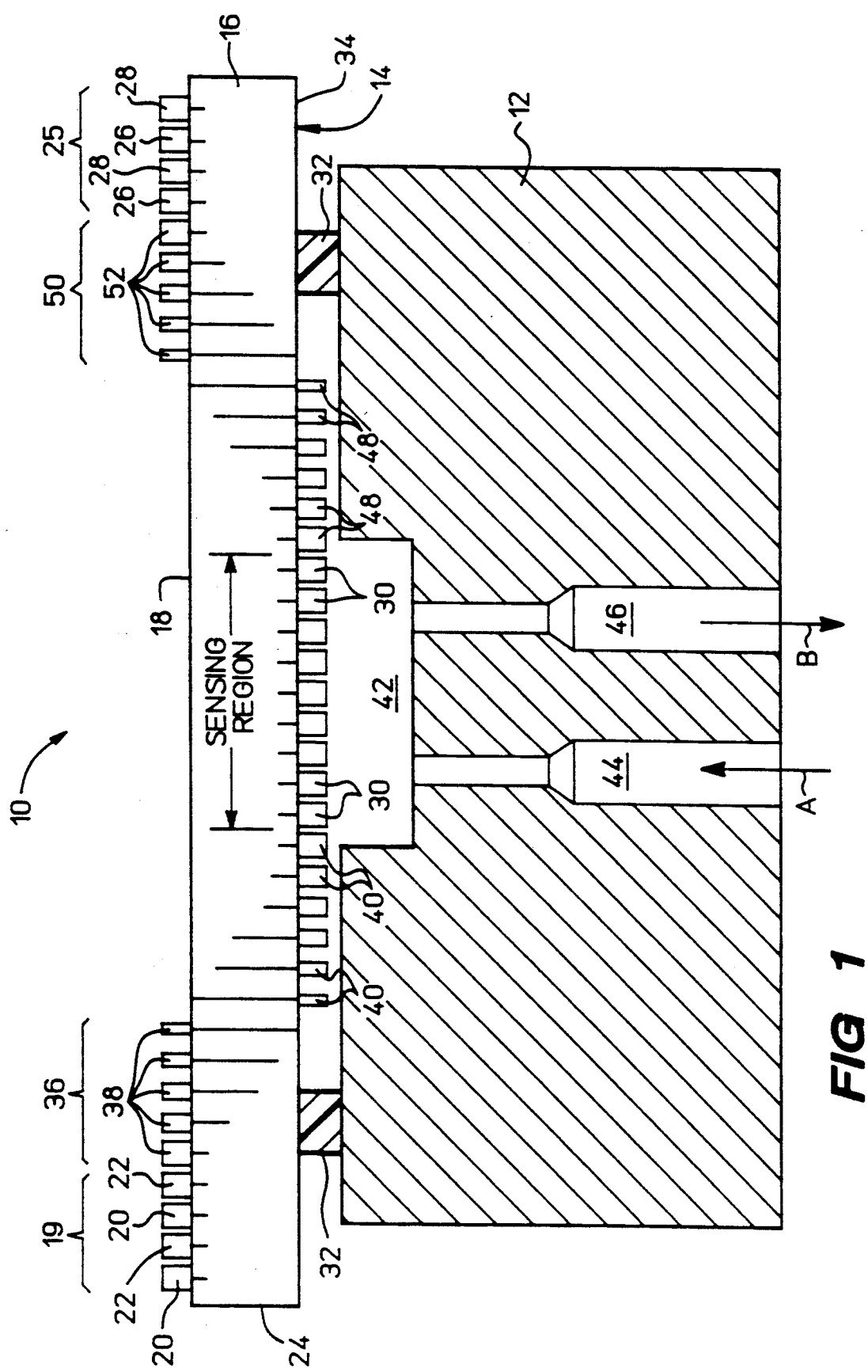
FIG. 1 is a side view of a first embodiment of a Surface Transverse Wave fluid sensing device having wave-trapping fingers that vary in width in accord with the present invention.

With reference to FIG. 1, a fluid sensor 10 includes a flow cell 12 and a Surface Transverse Wave (STW) device 14. The STW device includes a piezoelectric substrate 16 having a transduction surface 18 for the propagation of shear transverse, or shear horizontal, wave motion in which displacement of piezoelectric material is perpendicular to the direction of propagation and parallel to the substrate surface. The piezoelectric material may be quartz, $LiTaO_3$, $LiNbO_3$, or any other material known for use with STW devices. The piezoelectric substrate 16 is cut to couple energy from an input interdigital transducer 19 having electrode fingers 20 and 22 into shear transverse waves. The choice of substrate material and the cut are also selected to enable trapping of wave energy at the substrate surface 18.

Alternating electrode fingers 20 of the input interdigital transducer 19 are electrically connected and are interleaved with the electrode fingers 22. The electrode fingers are made of a conductive material, such as aluminum, which is deposited and photolithographically patterned on the transduction surface 18. The deposition of the conductive material which forms the electrode fingers 20 and 22, as well as other fingers to be described below, is provided by conventional methods, such as evaporation or sputter deposition. The electrode fingers have a typical thickness within the range of 0.01 micron to 1.0 micron. The width of an electrode finger may be within the range of 1 micron to 100 microns. An applied voltage difference between the electrode fingers 20 and the electrode fingers 22 produces an electric field that interacts electromechanically with the piezoelectric substrate 16 to launch surface transverse waves along a sensing region of the piezoelectric substrate. A grating of fingers, not shown, may be fabricated between the input interdigital transducer and a first edge 24 of the piezoelectric substrate 16.

An output interdigital transducer 25 having electrode fingers 26 and 28 is formed near the end of the substrate surface 18 opposite to the input interdigital transducer 19. In operation, an alternating voltage is supplied to the input interdigital transducer to provide an electric field between the electrode fingers 20 and 22. A stress field is generated by the electromechanical action of the piezoelectric substrate 16. Because of the particular crystalline structure of the piezoelectric substrate, this stress field generates shear transverse waves at a design frequency. The shear transverse waves propagate toward the output interdigital transducer and create an electric field between electrode fingers 26 and electrode fingers 28, producing an output signal.

Shear transverse waves have an inherent characteristic of diffracting into the bulk of the piezoelectric substrate 16 as the waves propagate from the input interdigital transducer 19 to the output interdigital transducer 25. However, it is known that periodic perturbations formed at the substrate surface will function to trap wave energy closer to the substrate surface. The periodic perturbations may be formed by cutting grooves into the piezoelectric substrate 16. Alternatively, an array of wave-trapping fingers may be fabricated utilizing the same photolithographical techniques used to deposit the electrode fingers 20, 22, 26 and 28 of the transducers. Wave-trapping fingers slow the shear transverse waves, thereby creating a decay of the wave function into the depth of the piezoelectric substrate 16. This "slowing effect" that creates the trapping is due to the multiple reflections from the individual fingers. Typically, the fingers are photolithographically patterned from a layer of metal, such as aluminum. Because metals are particularly dense, metallic fingers are thinner than functionally comparable wave-trapping fingers of other materials. In addition, metallic fingers short out the piezoelectric substrate 16 at the surface on which the fingers are formed, thereby reducing the stiffness of the substrate at that surface. This provides increased trapping of shear transverse waves. However, other materials may be utilized.

In operation, at least those wave-trapping fingers 30 within a sensing region of the piezoelectric substrate 16 are formed from a number of layers of material. As described above, the first material is preferably a metal that can short out the piezoelectric substrate at its surface to enhance trapping of shear transverse waves. A second layer is an attachment layer that may be deposited by sputtering or by evaporation. For example, a layer having a thickness within the order of 10 to 1000 angstroms may be formed to protect the metallic layer of the fingers 30 from attack by chemicals. This protective layer may also cover the substrate surface 34 where the surface is exposed by spacings between the wave-trapping fingers 30. For embodiments that are to serve as chemical sensors, a chemically reactive layer is then deposited. The chemically reactive layer is chosen to preferentially react with a constituent of a fluid under test.

Silicon dioxide may be used as an attachment layer, since a large amount of literature is available regarding binding various chemically selective compounds to silicon dioxide. Other layers may also be used. For example, a uniform grounded metallic layer may be formed either above or below the fingers 30 to shield propagating shear transverse waves from the conductivity of the liquid or gas under test.

Mounted to the STW device 14 is the flow cell 12. In the prior art, the flow cell was mounted to the transduction surface 18 of the piezoelectric substrate 16. Therefore, an important concern was the effect of a fluid under test on the electrode fingers 20, 22, 26 and 28 of the opposed interdigital transducers 19 and 25. A fluid may cause corrosion of the electrode fingers or may electrically short electrode fingers 20 of the input interdigital transducer to the other electrode fingers 22 of the same transducer. To prevent corrosion, electrical shorting or any other adverse effect of the fluid, a gasket was used to restrict the flow of the fluid to a controlled area that excluded the interdigital transducers. A problem in prior art devices which sealed the transducers from the flow of fluid was selecting the optimal placement of the seal and selecting the material for making the seal. A seal, such as a gasket 32 shown in FIG. 1, will reflect and/or absorb shear transverse wave energy from the piezoelectric substrate 16 if the gasket is placed on the transduction surface 18. The resulting attenuation of energy reduces the sensitivity of the fluid sensor.

The present invention overcomes this structure-imposed attenuation of a seal member by providing a controlled diffraction of wave energy into the piezoelectric substrate 16 for the tight trapping of the energy to a sensing surface 34 and by mounting the flow cell 12 to the sensing surface 34. "Tight trapping" is referred to herein as a trapping of shear transverse wave energy to a maximum depth of three wavelengths of the propagating waves. The series of vertical lines extending downwardly from the transduction surface 18 and upwardly from the sensing surface 34 is provided as a graphical illustration of the depth of wave penetration, although the bars are not intended to be proportional representations of penetration. Typically, the number of wave-trapping fingers greatly exceeds the number shown in FIG. 1.

A first array 36 of wave-trapping fingers is disposed on the transduction surface 18 immediately adjacent to the input interdigital transducer 19. To maximize performance, the period of the fingers of the first array 36 is fixed and is equal to the period of the interdigital transducers 19 and 25. However, the widths of adjacent wave-trapping fingers 38 gradually decrease with departure from the input interdigital transducer 19, thereby allowing increased penetration of wave energy into the piezoelectric substrate 16. Preferably, the first array 36 terminates upon penetration of the energy throughout the bulk of the piezoelectric substrate.

The diffraction of wave energy into the bulk of the piezoelectric substrate 16 allows a second array of wave-trapping fingers to draw the energy to the sensing surface 34. A first series of wave-trapping fingers contains fingers 40 that gradually increase in width for tighter trapping of energy. A maximum width is reached at the fingers 30 within the sensing region of the piezoelectric substrate 14. The flow cell 12 defines a flow chamber 42 that generally corresponds with the sensing region. As indicated by arrow A, a fluid under test is introduced into an input passageway 44. Typically, the fluid is a liquid having a constituent that is of interest. The liquid then exits through an output passageway 46, as indicated by arrow B. The gasket 32 prevents escape of the liquid.

In the same manner that the series of wave-trapping fingers 40 draw wave energy increasingly closer to the sensing surface 34, a series of fingers 48 on the opposite end of the sensing region relaxes the trapping for the transfer of energy to the transduction surface 18. The wave-trapping fingers 30 within the sensing region are relatively wide to maximize surface trapping. The wave-trapping fingers 48 within the second series taper in width while maintaining the same periodicity. A third array 50 of wave-trapping fingers 52 recaptures the wave energy to the transduction surface 18. The fingers 52 increase in width in correspondence with approach to the output interdigital transducer 25. This ensures an efficient electromechanical coupling between the transducer 25 and the piezoelectric substrate 16.

For a given finger grating periodicity ($p=0.475$ times the wavelength ($\lambda$) of STWs and a given grating height ($h=0.01p$), the following results were computationally determined for different ratios ($r$) of finger width-to-p:

CASE 1 - Where $r=0.4$, the STW power decays to 25% of its substrate surface value at a depth of $7\lambda$;

CASE 2 - Where $r=0.5$, the STW power decays to 25% of its substrate surface value at a depth of $6\lambda$;

CASE 3 - Where $r=0.6$, the STW power decays to 25% of its substrate surface value at a depth of $4\lambda$;

CASE 4 - Where $r=0.8$, the STW power decays to 25% of its substrate surface value at a depth of $3\lambda$; and CASE 5 - Where $r=1.0$, the STW power decays to 25% of its substrate surface value at a depth of $2\lambda$.

In operation, the input interdigital transducer 19 launches shear transverse waves in the direction of the output interdigital transducer 25. Because the first array 36 of wave-trapping fingers 38 taper in width, the wave energy diffracts into the bulk of the piezoelectric substrate 16. The diffraction is controlled by the wave-trapping fingers 38.

The series of wave-trapping fingers 40 that is on the end of the sensing region associated with the input interdigital transducer 19 captures the wave energy for tight surface trapping by the central fingers 30 that are of uniform width and height. It is within the region associated with the uniform fingers 30 that the sensitivity of the STW device 14 is most critical. A second series of wave-trapping fingers 48 then relax trapping for recapture by a third array 50 that maximizes electromechanical coupling to the output interdigital transducer 25.

Figure 2:
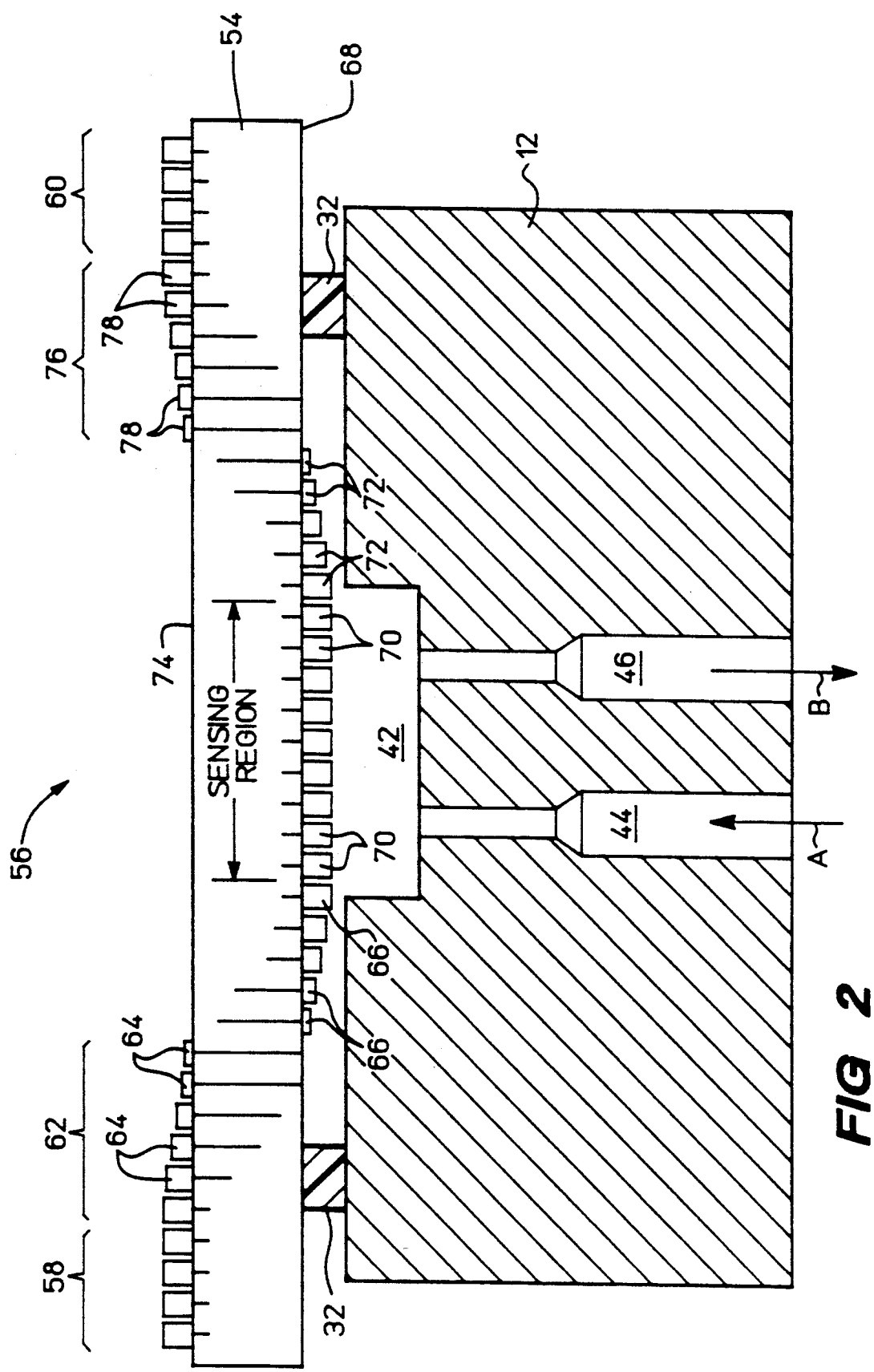
FIG. 2 is a side view of an alternative Surface Transverse Wave fluid sensing device having wave-trapping fingers that vary in thickness in accord with the present invention.

Referring now to FIG. 2, the height, or thickness, of fingers also affect the penetration of shear transverse waves into a piezoelectric substrate 54 of an STW fluid sensor 56. The piezoelectric substrate 54 includes an input interdigital transducer 58 and an output interdigital transducer 60. Transmitting interdigital transducer 58 launches shear transverse waves that are controllably diffracted into the bulk of the piezoelectric substrate. The control of this diffraction is provided by a first array 62 of wave-trapping fingers 64 that gradually taper in height. As with the tapering width described above, the change in height of the fingers 64 should be a gradual taper. Abrupt transitions create reflection-inducing discontinuities that affect the performance of the fluid sensor 56. The wave-trapping fingers immediately adjacent to the interdigital transducer should have a height generally equivalent to that of the electrode fingers of the transducer. This ensures an effective coupling of power from the transducer to the piezoelectric substrate 54. The bars extending downwardly from the fingers 64 are provided as illustration of increasing penetration of energy with a reduction in height.

In the same manner that the wave-trapping fingers 64 relax the trapping of wave energy with departure from the input interdigital transducer 58, wave-trapping fingers 66 on a sensing surface 68 gradually increase in height to tightly trap the wave energy with approach to a sensing region of the piezoelectric substrate. Within the sensing region, the energy is tightly trapped by fingers 70 having uniform height, width and periodicity. A fluid under test enters a flow cell 12 at an input passageway 44 to a flow chamber 42, whereafter the fluid exits through an output passageway 46. A gasket 32 restricts the flow of liquid.

Wave-trapping fingers 72 then allow a second gradual decay of the waves, but this gradual decay is a diffraction of waves toward the transduction surface 74. The diffracting waves are captured by a third array 76 of wave-trapping fingers 78 that draw the wave energy to the surface for efficient decoupling of the energy by the output interdigital transducer 60.

A problem with the embodiment of FIG. 2 involves fabrication of the STW fluid sensor 56. Preferably, all of the wave-trapping fingers 66, 70 and 72 on the sensing surface 68 would be formed in a single fabrication step. This would require controlling the rate of material deposition as a function of the position on the sensing surface. For example, in deposition by evaporation, a pair of wires could be suspended away from the piezoelectric substrate 54 directly adjacent to the outermost fingers 66 and 72. Each wire would function as a shadow mask for the tapering of finger height. Evaporated material would then be shadowed and a gradual variation of metal height would occur. A similar fabrication technique could be used in providing the tapering of finger height within the first array 62 and the third array 76.

An alternative would be to employ a number of steps to selectively build fingers 66, 70 and 72. A first deposition would form the metal fingers at a uniform height, whereafter selected fingers, such as the fingers 70 within the sensing region, would receive a second layer of the same metallic material. The number of steps would then depend upon the number of heights. For example, concentrating on the fingers 66 on the input end of the sensing region, five steps would be required in forming these five fingers of different heights.

For a given finger grating periodicity ($p = 0.475\lambda$) and a given ratio of finger width-to-p ($r = 0.5$), the following results were computationally determined for different uniform heights within a grating:

CASE 6 - Where $h=0$, the STW power penetrates through the entire substrate, i.e., there is no surface trapping;

CASE 7 - Where $h=0.01p$, the STW power decays to 25% of its substrate surface value at a depth of $6\lambda$;

CASE 8 - Where $h=0.02p$, the STW power decays 25% of its substrate surface value at a depth of $4\lambda$; and CASE 9 - Where $h=0.03p$, the STW wavelength decays to 25% of its substrate surface value at $3\lambda$.

It is possible to combine the varying height of FIG. 2 and the varying width of FIG. 1 to provide a fluid sensor that would allow greater control of gradual transitions in wave penetration. Disregarding difficulties in fabrication, this would be a preferred structure since gradual variations avoid reflections that occur when waves encounter abrupt discontinuities in structural aspects such as height or width.

A less desirable method of controlling the depth of penetration is to vary the periodicity of the wave-trapping fingers of an STW device. An increase in the period of the fingers increases the surface trapping below the stop band edge, while a decrease allows greater penetration. However, the period is preferably fixed, so as to restrict the effects of Bragg scattering to a small range of frequencies.

Figure 3:
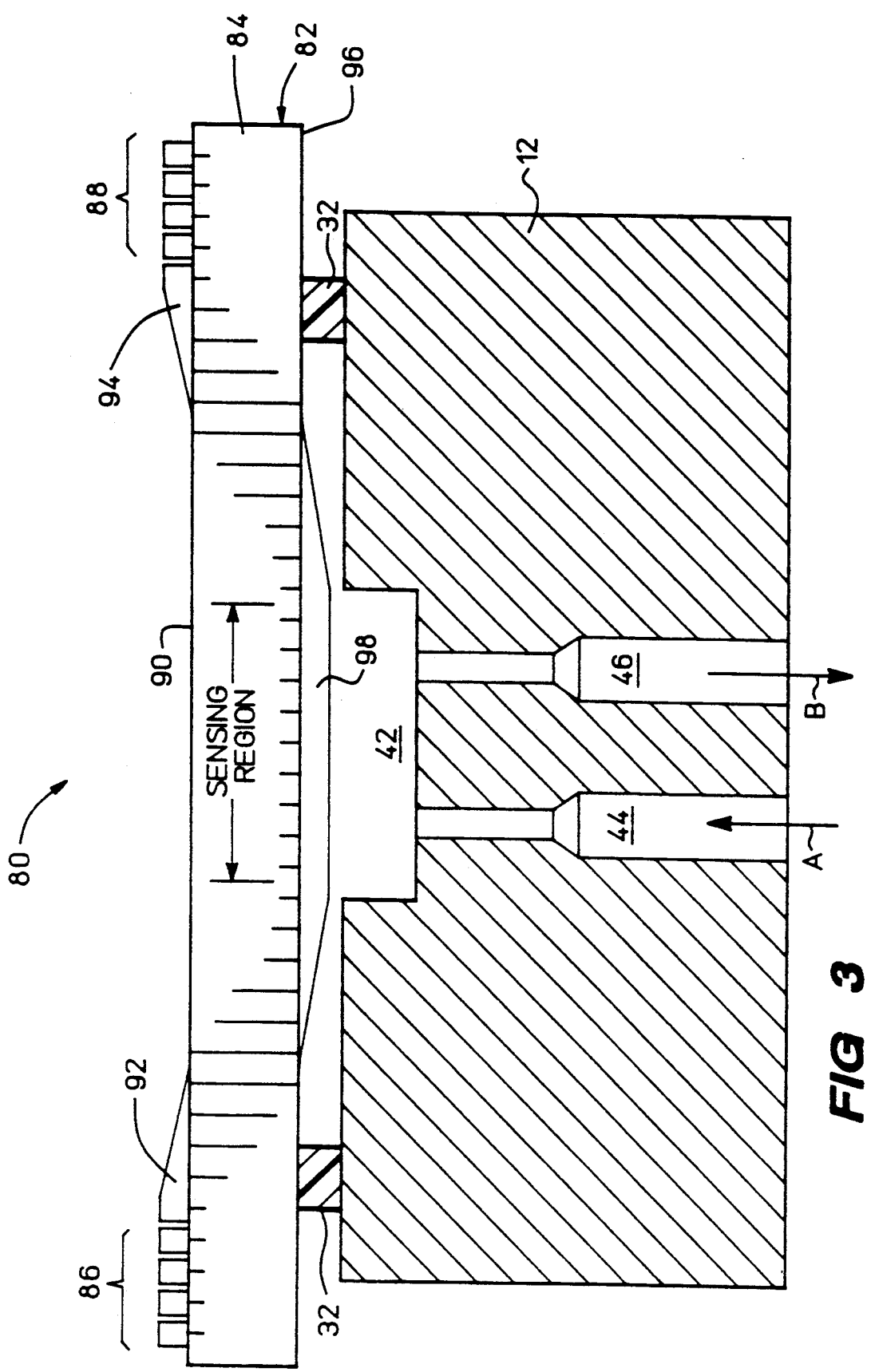
FIG. 3 is a side view of a Love Wave fluid sensing device having wave-trapping plates that vary in thickness in accord with the present invention.

Another embodiment of the present invention is illustrated in FIG. 3. A fluid sensor 80 includes a flow cell 12 that is identical to the one described above, but the flow cell is coupled to a Love Wave (LW) device 82. A piezoelectric substrate 84 has an input interdigital transducer 86 and an output interdigital transducer 88. The transducers 86 and 88 are on a transduction surface 90 of the piezoelectric substrate. Between the transducers 86 and 88 are first and second wave-trapping plates 92 and 94. While plates of an LW device are known to be less effective at trapping wave energy than the periodic perturbations of an STW device, the plates do have a slowing effect on the shear transverse waves, thereby restricting the tendency of such waves to diffract into the entirety of the piezoelectric substrate 84. However, in the present invention the first wave-trapping plate 92 is used to allow diffraction of the waves into the entirety of the substrate, but to do so in a controlled manner.

The first wave-trapping plate is tapered in thickness to selectively relax the trapping of wave energy. The reduced thickness at the end of the plate opposite to the input interdigital transducer 86 allows a gradual increase in penetration, as graphically indicated by the bars extending from the plate into the piezoelectric substrate 84.

On a sensing surface 96 opposite to the transduction surface 90 is another wave-trapping plate 98. This wave-trapping plate has a maximum thickness at the sensing region of the piezoelectric substrate 84. Opposite ends of the plate taper in thickness. On the input end of the wave-trapping plate 98 surface trapping is gradually increased by the thickening of the plate with approach to the sensing region. At the opposite end, the thickness is gradually reduced to allow a controlled diffraction of shear transverse waves that are recaptured at the transduction surface 90 by the second wave-trapping plate 94. The varying thickness of the second plate 94 provides increased efficiency in the electromechanical coupling of the piezoelectric substrate 84 to the output transducer 88.

As in the embodiments described above, the wave-trapping plates 92, 94 and 98 are preferably made of metal, but this is not critical. Any material which has a lower acoustic shear wave velocity than the piezoelectric substrate 84 may be used. Typically, the plate 98 at the sensing region is a multi-layered structure having a layer that is chemically reactive to a constituent of interest within a fluid under test.

Yet another embodiment would be to use a grating of wave-trapping fingers on one side of a piezoelectric substrate and to use a wave-trapping plate on the opposite side.

In all of the embodiments described above, the flow cell 12 is coupled to a side of the piezoelectric substrate that is opposite to the input and output transducers. The sealing members, which have been described as being gaskets, are connected to the piezoelectric substrate beyond the extent of the wave-trapping structures. Thus, the sealing member is not in contact with an area of a surface to which propagating waves are trapped. This substantially reduces the importance of the choice of materials in constructing a fluid seal. In the prior art, the main concern was providing a seal member which was sufficiently compliant to prevent unacceptable levels of attenuation. The present invention allows a focus to be upon providing a reliable fluid-tight seal using a material which is chemically resistant to a particular fluid under test.

We claim:

1. A sensing device for use in testing with fluids comprising,
   a substrate adapted to propagate shear transverse waves, said substrate having opposed first and second surfaces, said second surface having a sensing region,
   an input means on said first surface for launching shear transverse waves, said waves having a tendency to diffract from the first surface into the bulk of said substrate,
   an output means on said first surface for receiving said waves,
   first wave-trapping means having a first section on said first surface for allowing increasing diffraction of waves into the bulk of said substrate with departure from said input means and having a second section for recapturing wave energy with approach to said output means,
   second wave-trapping means on said sensing region of said second surface for selectively tightening and relaxing trapping of said waves which are diffracting with said departure from said input means, said second wave-trapping means having a dimensional configuration to relax trapping of said waves for said recapturing of wave energy by said second section of said first wave-trapping means, and
   means for applying a fluid under test to said sensing region of said second surface.

2. The device of claim 1 wherein said first and second sections of said first wave-trapping means are first and second gratings of fingers, respectively, each finger having a width substantially parallel to a direction of wave propagation from said input means, said widths of at least some of said fingers of said first grating decreasing with departure from said input means, said widths of at least some of said fingers of said second grating increasing with approach to said output means.

3. The device of claim 1 wherein said first and second sections of said first wave-trapping means are first and second gratings of fingers, respectively, each finger having a height from said substrate, said heights of at least some of said fingers of said first grating decreasing with departure from said input means, said heights of at least some of said fingers of said second grating increasing with approach to said output means.

4. The device of claim 1 wherein said second wave-trapping means is a grating of fingers disposed on said sensing region of said second surface, with said fingers tapering dimensionally with respect to at least one of finger width and finger height, said fingers increasing dimensionally from minimums at opposed ends of said grating of fingers to a maximum between said opposed ends.

5. The device of claim 1 wherein said first and second sections of said wave-trapping means are first and second plates, respectively, at least a portion of said first plate decreasing in thickness with departure from said input means, at least a portion of said second plate increasing in thickness with approach to said output means.

6. The device of claim 5 wherein said second wave-trapping means is a third plate having a minimum thickness at opposed ends and a maximum thickness along a central region.

7. The device of claim 1 wherein said means of applying a fluid is a flow cell coupled to said second surface of said substrate, said flow cell including a seal in contact with said second surface in spaced apart relationship with said sensing region.

8. A Surface Transverse Wave device for use in testing with fluids comprising,
   piezoelectric means for propagating shear transverse waves, said piezoelectric means having a substrate having opposed transduction and sensing sides, said piezoelectric means further having an input transducer on said transduction side to launch said waves and an output transducer on said transduction side to receive said waves, said input transducer spaced apart from said output transducer,
   means for applying a fluid to said sensing side of said substrate,
   first wave-trapping means on said transduction side of said substrate proximate to said input transducer for guiding transfer of wave energy from said transduction side to said sensing side, said first wave-trapping means including a first grating of fingers having heights and widths, at least one of said heights and widths varying from finger-to-finger so as to provide said guiding of wave energy,
   second wave-trapping means on said sensing side within a sensing region of said substrate to trap wave energy received from said input transducer on said transduction side, said second wave-trapping means including a second grating of fingers, and
   third wave-trapping means on said transduction side proximate to said output transducer for recapturing wave energy from said sensing side, said third wave-trapping means including a third grating of fingers having heights and widths, at least one of said heights and widths varying from finger-to-finger for said recapturing of wave energy.

9. The device of claim 8 wherein said means for applying a fluid is a flow cell having a seal fixed to said sensing side of said substrate in spaced relationship to said second wave-trapping means.

10. The device of claim 8 wherein said first grating of fingers includes a gradual decrease in finger width in correspondence with increasing distance from said input transducer and wherein said third grating of fingers includes a gradual decrease in finger width in correspondence with increased distance from said output transducer.

11. The device of claim 8 wherein said first grating of fingers includes a gradual decrease in finger height in correspondence with increasing distance from said input transducer and wherein said third grating of fingers includes a gradual decrease in finger height in correspondence with increased distance from said output transducer.

12. The device of claim 8 wherein said second grating of fingers has first and second ends, each having fingers having widths less than the widths of fingers spaced apart from said first and second ends.

13. The device of claim 9 wherein said seal is a gasket framing said sensing region.

14. A Love Wave device for use in testing with fluids comprising, piezoelectric means for propagating shear transverse waves, said piezoelectric means having a substrate having opposed transduction and sensing sides, said transduction side having an input transducer to launch said waves and an output transducer to receive said waves, said input transducer spaced apart from said output transducer, means for applying a fluid to said sensing side of said substrate, a first wave-trapping plate on said transduction side proximate to said input transducer, said first wave-trapping plate diminishing in thickness at a plate end opposite to said input transducer, a second wave-trapping plate on said sensing side for surface trapping of wave energy from said input transducer, and a third wave-trapping plate on said transduction side proximate to said output transducer, said third wave-trapping plate diminishing in thickness at a plate end opposite to said output transducer, said first and third wave-trapping plates being spaced apart.

15. The device of claim 14 wherein said means for applying a fluid is a flow cell having a seal fixed to said sensing side of said substrate in spaced relationship to said second wave-trapping plate.

16. The device of claim 14 wherein said input and output transducers are each interdigital transducers.

17. The device of claim 14 wherein said second wave-trapping plate has opposed ends, said opposed ends each being gradually tapered in thickness.

* * * * *

UNITED STATES PATENT AND TRADEMARK OFFICE
CERTIFICATE OF CORRECTION

PATENT NO. : 5,321,331
DATED : June 14, 1994
INVENTOR(S) : Richard L. Baer, et. al.

It is certified that error appears in the above-indentified patent and that said Letters Patent is hereby corrected as shown below:

Column 4, line 27, "transducer" should read -- transducers--;

Column 10, lines 10-11, "decays 25%" should read -- decays to 25% --;

Signed and Sealed this

First Day of November, 1994

Attest:

BRUCE LEHMAN

Attesting Officer

Commissioner of Patents and Trademarks